United States Patent
Pavliv et al.

(10) Patent No.: US 10,456,380 B2
(45) Date of Patent: *Oct. 29, 2019

(54) COMPOSITIONS AND METHODS OF TREATING MUSCULAR DYSTROPHY WITH THROMBOXANE-$A_2$ RECEPTOR ANTAGONISTS

(71) Applicants: Cumberland Pharmaceuticals Inc., Nashville, TN (US); Vanderbilt University, Nashville, TN (US)

(72) Inventors: Leo Pavliv, Cary, NC (US); James West, Nashville, TN (US); Ines Macias-Perez, Mt. Juliet, TN (US); Erica Carrier, Nashville, TN (US)

(73) Assignees: CUMBERLAND PHARMACEUTICLS INC., Nashville, TN (US); VANDERBILT UNIVERSITY, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/240,368

(22) Filed: Jan. 4, 2019

(65) Prior Publication Data

US 2019/0142807 A1    May 16, 2019

Related U.S. Application Data

(63) Continuation of application No. 16/050,798, filed on Jul. 31, 2018, now abandoned, which is a continuation of application No. 15/592,727, filed on May 11, 2017, now Pat. No. 10,064,845.

(60) Provisional application No. 62/334,748, filed on May 11, 2016.

(51) Int. Cl.
*A61K 31/422*    (2006.01)

(52) U.S. Cl.
CPC ................................. *A61K 31/422* (2013.01)

(58) Field of Classification Search
None
See application file for complete search history.

(56) References Cited

U.S. PATENT DOCUMENTS

| | | |
|---|---|---|
| 4,258,058 A | 3/1981 | Witte et al. |
| 4,416,896 A | 11/1983 | Nakane et al. |
| 4,443,477 A | 4/1984 | Witte et al. |
| 4,537,981 A | 8/1985 | Snitman et al. |
| 4,663,336 A | 5/1987 | Nakane et al. |
| 4,752,616 A | 6/1988 | Hall et al. |
| 4,839,384 A | 6/1989 | Ogletree |
| 4,977,174 A | 12/1990 | Stein et al. |
| 5,066,480 A | 11/1991 | Ogletree et al. |
| 5,100,889 A | 3/1992 | Misra et al. |
| 5,128,359 A | 7/1992 | Bru-Magniez et al. |
| 5,312,818 A | 5/1994 | Rubin et al. |
| 5,399,725 A | 3/1995 | Poss et al. |
| 5,506,248 A | 4/1996 | Nikfar et al. |
| 6,509,348 B1 | 1/2003 | Ogletree |
| 7,785,891 B2 | 8/2010 | Phillips et al. |
| 8,299,097 B2 | 10/2012 | Boyce |
| 9,693,998 B2 | 7/2017 | Pavliv et al. |
| 10,064,845 B2 * | 9/2018 | Pavliv .................. A61K 31/422 |
| 2006/0009496 A1 | 1/2006 | Oates et al. |
| 2009/0012115 A1 | 1/2009 | Phillips et al. |
| 2009/0012136 A1 | 1/2009 | Stephens et al. |
| 2009/0022729 A1 | 1/2009 | Mackman et al. |
| 2017/0000771 A1 | 1/2017 | Pavliv |
| 2017/0258771 A1 | 9/2017 | Pavliv et al. |
| 2017/0312255 A1 | 11/2017 | Pavliv et al. |
| 2017/0319554 A1 | 11/2017 | Pavliv et al. |
| 2018/0050020 A1 | 2/2018 | Pavliv |

FOREIGN PATENT DOCUMENTS

| | | |
|---|---|---|
| EP | 0638310 A1 | 2/1995 |
| JP | H02273625 A | 11/1990 |
| WO | 2006132460 A1 | 12/2006 |
| WO | 2008137793 A1 | 11/2008 |
| WO | 2012009545 A1 | 1/2012 |

OTHER PUBLICATIONS

Montuschi, et al., "Isoprostanes: markers and mediators of oxidative stress," FASEB J. 2004;18(15):1791-800.
Nanji, A. et al. "Thromboxane Inhibitors Attenuate Inflammatory and Fibrotic Changes in Rat Liver Despite Continued Ethanol Administrtions," Alcoholism: Clinical and Experimental Research, vol. 37, No. 1, pp. 31-39, (2013).
Narisada, M et al., "S-1452, Shionogi domitroban, Anboxan®" pp. 1-14 (2004).
Peters, et al., "Acute hepatic failure: limitations of medical treatment and indications for liver transplantation," The Clinical Investigator, 1993, vol. 71, No. 11, pp. 875-881.
Pidgeon et al. "Intravascular thrombosis after hypoxia-induced pulmonary hypertension—Regulation by cyclooxygenase—2", Circulation, American Heart Association Inc., vol. 110, No. 17, pp. 2701-2707 (2004).
Rosado, E. et al, "Terutroban, a TP-Receptor Antagonsist, Reduces Portal Pressure in Cirrhotic Rats," Hepatology, Official Journal of the American Association for the Study of Liver Diseases, pp. 1-12 (2013).
Rosenfeld, L., et al, "Ifetroban Sodium: An Effective TxA2/PGH2 Receptor Antagonist," Cardiovascular Drug Reviews, vol. 19, No. 2, pp. 97-115 (2001).
Soper, CP, et al., "Amelioration of hepatorenal syndrome with selective endothelin-A antagonist," Lancet. 1996;347:1842-3.
Touchberry et al. "Cardiac Thromboxane A2 Receptor Activation Does Not Directly Induce Cardiomyocyte Hypertrophy but Does Cause Cell Death that is Prevented with Gentamicin and 2-APB," BMC Pharmacology and Toxicology, vol. 15, pp. 1-12 (2014).

(Continued)

*Primary Examiner* — Brian J Davis
(74) *Attorney, Agent, or Firm* — Vivicar Law, PLLC

(57) ABSTRACT

The present invention is directed to methods of treating and/or ameliorating muscular dystrophy and/or treating cardiomyopathy in muscular dystrophy patients by administration of a therapeutically effective amount of a thromboxane $A_2$ receptor antagonist.

20 Claims, 16 Drawing Sheets

(56) References Cited

OTHER PUBLICATIONS

Wacker et al. "Inhibition of Thromboxane A_2-Induced Arrhythmias and Intracellular Calcium Changes in Cardiac Myocytes by Blockade of the Inositol Trisphosphate Pathway," The Journal of Pharmacology and Experimental Therapeutics, vol. 331, No. 3, pp. 917-924 (2009).
Wasserman, et al. "SKF 88046," Smith Kline & West Laboratories, Pharmacologist 25(3):117 Abs, (1983).
West et al., "Antagonism of the Thromboxane-Prostanoid Receptor is Cardioprotective against Right Ventricular Pressure Overload," Pulmonary Circulation, vol. 6, No. 2, pp. 211-223 (2016).
Zhang et al. "COX-2 Dependent Cardiac Failure in Gh/tTG Transgenic Mice," Circulation Research; Journal of the American Heart Association, vol. 92, pp. 1153-1161 (2003).
Bauer et al., "Pathophysiology of isoprostanes in the cardiovascular system: implications of isoprostane-mediated thromboxane A2 receptor activation," British Journal of Pharmacology (2014), 171, pp. 3115-3131.
Acquaviva, A., et al., "Signaling pathways involved in isoprostane-mediated fibrogenic effects in rat hepatic stellate cells," Free Radical Biology and Medicine, vol. 65, pp. 201-207 (2013).
Amrstrong, R. et al., "Competitive antagonism at thromboxane receptors in human platelets," Brit. J. Pharmacol. 84 (3):595-607 (1985).
Angeli, P., et al. "Reversal of type 1 hepatorenal syndrome with the administration of midodrine and octreotide," Hepatology (1999) 29(6):1690-7.
Bianchetti, A. et al., "Pharmacological Actions of Levallorphan Allyl Bromide (CM 32191), A New Peripheral Narcotic Antagonist," Life Sci. 31, pp. 2261-2264 (1982).
Boland et al., "Skeletal, Cardiac, and Smooth Muscle Failure in Duchenne Muscular Dystrophy," Pediatric Neurology, vol. 14, No. 1, pp. 7-12 (1996).
Borgdorff, MA et al., "Sildenafil treatment in established right ventricular dysfunction improves diastolic function and attenuates interstitial fibrosis independent from afterload" Am J Physiol Heart Circ Physiol 307, pp. H361-H369 (2014).
Bresnahan, B., et al. "Mesangial Cell Immune Injury," J. Amer. Society of Nephrology, 1991, pp. 1041-1047.
Brittain, R.T. et al., "AH 23848: A Thromboxane Receptor-Blocking drug that can Clarify the Pathophysiologic Role of Thromboxane A2," Circulation 72(6)1208-1218 (1985).
Bruggeman, L.A., et al. "Thromboxane stimulates synthesis of extracellular matrix proteins in vitro" Am. J. Physiol. 261, F488-F494 (1991).
Byland, E. et al, "ICI 185282: A Selective, Potent Thromboxane A2 Receptor Antagonist on Smooth Muscle," Brit. J. Pharmacol. 90 (Proc. Suppl):228 P-Abs, (1985).
Carrier et al., "Preliminary Results of Thromboxane-Prostanoid Receptor Antagonism in Mouse Models of Muscular Dystrophy," American Journal of Respiratory and Critical Care Medicine, vol. 193, A7213 (2016).
Cathcart et al. "Cyclooxygenase—2 linked attenuation of hypoxia—induced pulmonary hypertension and intravascular thrombosis", The Journal of Pharmacology and Experimental Therapeutics, vol. 326, No. 1, pp. 51-58 (2008).
Cediel, E., et al. "AT-1 receptor antagonism modifies the mediation of endothelin-1, thromboxane A2, and catecholamines in the renal constrictor response to angiotensin II," Kidney International (2005) 67, pp. 1-10.
Cediel, et al., "AT-1 receptor antagonism modifies the mediation of endothelin-1, thromboxane A2, and catecholamines in the renal constrictor response to angiotensin II," 2005, Kidney International, vol. 67, pp. S3-S9.
Comporti, et al., "Isoprostanes and hepatic fibrosis," Mol Aspects Med. 2008;29(1-2):43-9.
Comporti, M. et al., "F2-isoprostanes stimulate collagen synthesis in activated hepatic stellate cells: a link with liver fibrosis?" Laboratory Investigation, vol. 85, pp. 1381-1391, (2005).
Cracowski, et al., "Increased formation of F(2)-isoprostanes in patients with severe heart failure," Heart. 2000;84 (4):439-40.
Dockens, R., et al, "Disposition of Radiolabeled Ifetroban in Rats, Dogs, Monkeys, and Humans," Drug Metabolism and Disposition, 2000, vol. 28 No. 8; pp. 973-980.
Dogan et al. "Thromboxane A_2 Receptor Mediation of Calcium and Calcium Transients in Rat Cardiomyocytes," Life Sciences; Elsevier; vol. 60, No. 12, pp. 943-952 (1997).
Dogne, J-M., et al., "Recent developments of thromboxane modulators," Exp. Opin. Ther. Patents 11: 1663-1675 (2001).
Donovan, JP., et al. "Cerebral edema and increased intracranial pressure in chronic liver disease," Lancet,1998;351 (9104):719-21.
Dr. G. Wright, "Hepatic Encephalopathy; The role of Inflammation, Ammonia and Aquaporin Expression in the Pathogenesis of Cerebral Oedema," Liver failure group, The Institute of Hepatology, University College London, 2009, pp. 1-292.
Fanelli, F., et al. "Management of refractory hepatic encephalopathy after insertion of TIPS: long-term results of shunt reduction with hourglass-shaped balloon-expandable stent-graft." Am J Roentgenol. 2009;193(6):1696-702.
Fevery J, et al., "Reversal of hepatorenal syndrome in four patients by peroral misoprostol (prostaglandin E1 analogue) and albumin administration," J Hepatol. 11(2):153-8 (1990).
Ford-Hutchinson, A.W., et al. "The pharmacology of L-670,596," Can. J. Physiol. Pharmacol., 1989, 67:989-993.
Francois et al., "A role for the thromboxane receptor in L-NAME hypertension," Am. J. Physiol. Renal. Physiol., vol. 295, pp. 1096-1102 (2008).
Francois et al., "Prostacyclin protects against elevated blood pressure and cardiac fibrosis", Cell Metabolism, vol. 2, No. 3, pp. 201-207 (2005).
Francois et al., "Role for Thromboxane Receptors Angiotensin-II-Induced Hypertension" Hypertension, 43:364-369 (2004).
Gardi, C. et al., "F2-isoprostane receptors on hepatic stellate cells" Laboratory Investigation, vol. 88, pp. 124-131 (2007).
Gelosa, P., et al. "Terutroban, a thromboxane/prostaglandin endoperoxide receptor antagonist, prevents hypertensive vascular hypertrophy and fibrosis," Am J Physiol Heart Circ Physiol 300: pp. H762-H768, Dec. 10, 2010.
Gentilini, P., et al., "Renal effects of a thromboxane (TX) A2 receptor antagonist (ONO-3708) in cirrhotics with ascites (C)," Journal of Hepatology, vol. 11, p. S25 (1990).
Gluud, L.L., et al. "Systematic review of randomized trials on vasoconstrictor drugs for hepatorenal syndrome," Hepatology. 2010 51:576-584.
Grandi, AM et al., "Aldosterone Antagonist Improves Diastolic Function in Essential Hypertension," Hypertension 40, pp. 647-652 (2002).
Grosso, et al., "Isoprostanes in dystrophinopathy: Evidence of increased oxidative stress," Brain Dev. 2008;30 (6):391-5.
Guevara M, et al. "Hepatorenal syndrome," Dig Dis. 2005;23(1):47-55.
Guevara M., et al., "Hepatorenal syndrome," Int J Biochem Cell Biol. 2005;37(1):22-6.
Hall, R.A. et al., "Pharmacology of L-655,240 (3-[1-(4-chlorobenzyl)-5-fluoro-3-methyl-indol-2-yl] 2,2-dimethylpropanoic acid); a potent, selective thromboxane / prostaglandin endoperoxide antagonist," Eur. J. Pharmacol. 135(2)193-201 (1987).
Hara et al. "Augmented Cardiac Hypertrophy in Response to Pressue Overload in Mice Lacking the Prostaglandin I_2 Receptor" Circulation, 112:84-92 (2005).
International Search Report and Written Opinion, dated Jul. 26, 2017, issued in connection with International Application No. PCT/US2017/032151.
International Search Report in International Application No. PCT/US15/31395, dated Aug. 10, 2015.
Jessup, C.L. et al., "ICI 159995: A Novel Thromboxane A2 Receptor Antagonist," Brit. J. Pharmacol. 86 (Proc. Suppl):808 P-Abs. (1985).

(56) References Cited

OTHER PUBLICATIONS

Jiang, Q et al., "Cardiovascular Phamtacology Inhibitory effect of ginsenoside Rb1 on calcineurin signal pathway in cardiomyocyte hypertrophy induced by prostaglandin F2alpha" Acta Pharmacologica Sinica 28, p. 1149-1154 (2007).

Kramer, H.J., et al, "Effect of Thromboxane A2 Receptor Blockade on Oliguric Ischemic Acute Renal Failure in Conscious Rats," J. Am. Soc. Nephrol., 1993 vol. 4 No. 1, pp. 50-57.

Kunapuli, P. et al. "Prostaglandin F2alpha (PGF2alpha) and the Isoprostane, 8, 12-iso-Isoprostane F2alpha-III, Induce Cardiomyocyte Hypertrophy," The Journal of Biological Chemistry, vol. 273, No. 35, pp. 22442-22452, (1998).

Kurokawa, S., et al. "Effect of inhaled KP-496, a novel dual antagonist of the cysteinyl leukotriene and thromboxane A2 receptors, on a bleomycin-induced pulmonary fibrosis model in mice" Pulmonary Pharmacology & Therapeutics, vol. 23, pp. 425-431 (2010).

Lenz K, et al. "Beneficial effect of 8-omithin vasopressin on renal dysfunction in decompensated cirrhosis," Gut. Jan. 1989;30(1):90-6.

Lenz K, et al. "Omipressin in the treatment of functional renal failure in decompensated liver cirrhosis. Effects on renal hemodynamics and atrial natriuretic factor," Gastroenterology. 1991;101(4):1060-7.

Lenz K, et al., "Enhancement of renal function with ornipressin in a patient with decompensated cirrhosis," Gut, 1985;26(12):1385-6.

Liu, T, et al. "Prostaglandin E2 deficiency causes a phenotype of aspirin sensitivity that depends on platelets and cysteinyl leukotrienes" Proc Natl Acad Sci USA. (2013) Abstract only.

Liu, T., et al. "Prostaglandin E2 deficiency causes a phenotype of aspirin sensitivity that depends on platelets and cysteinyl leukotrienes" PNAS, Early Edition, pnas.org/cgi/doi/10.1073/pnas.1313185110 (2013).

* cited by examiner (A) Vehicle-treated DKO – 10 weeks (B) Ifetroban-treated DKO – 10 weeks dSG KO-vehicle dSG KO-ifetroban

Fig. 10A
dSG-veh
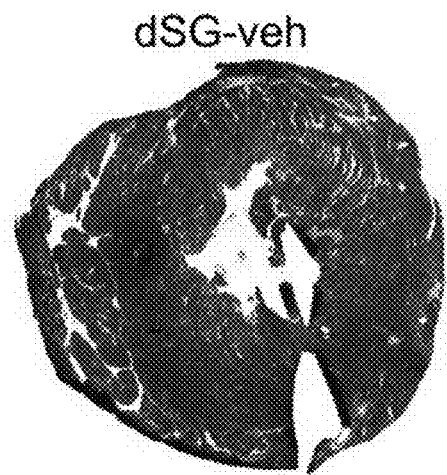
dSG-ifetroban
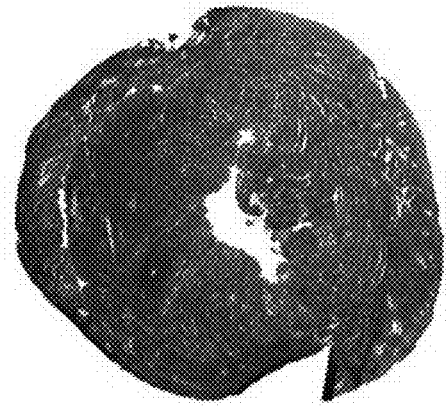
Fig. 10C
Fig. 10B
dSG-veh
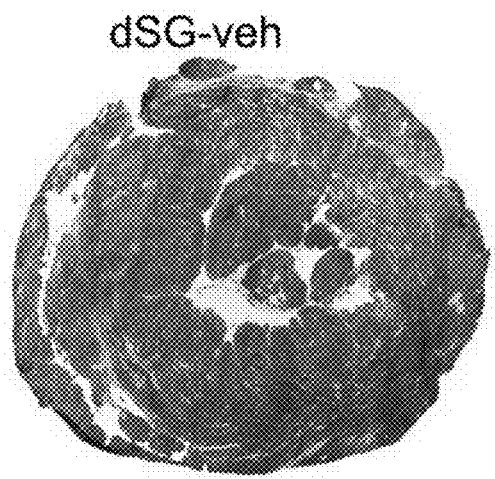
dSG-ifetroban
Fig. 10D

LV
Fig. 11A(1)  Fig. 11A(2)  Fig. 11A(3)  Fig. 11A(4)
 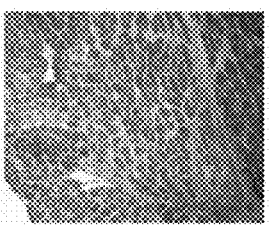 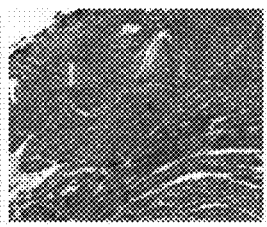 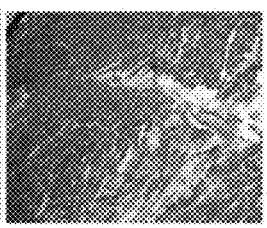
RV/Septum
Fig. 11B(1)  Fig. 11B(2)  Fig. 11B(3)  Fig. 11B(4)
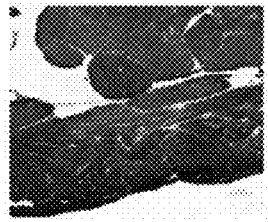   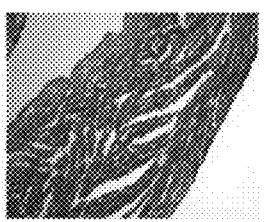
dSG KO-vehicle　　dSG KO-vehicle　　dSG KO-ifetroban　　dSG KO-ifetroban
Mouse #1　　　　　Mouse #2　　　　　Mouse #1　　　　　　Mouse #2

WT1 Fig. 12A
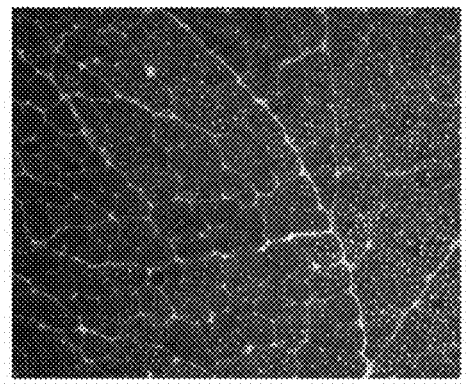
dSG KO-vehicle Fig. 12B
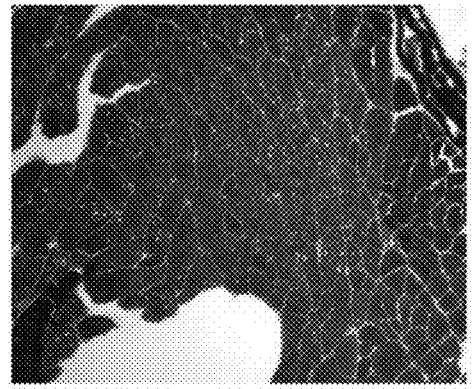
WT2 Fig. 12C
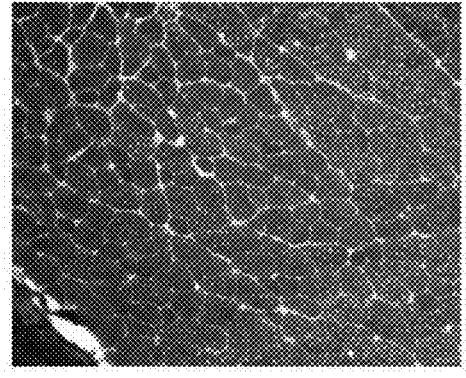
dSG KO-ifetroban Fig. 12D
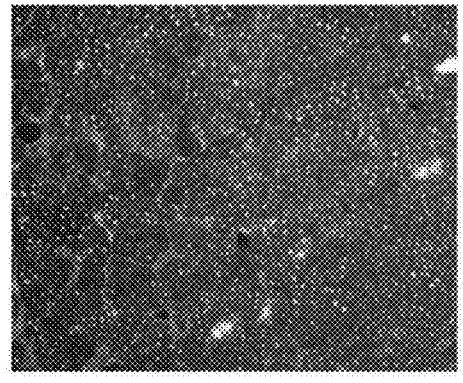

Fig. 13A  Fig. 13B
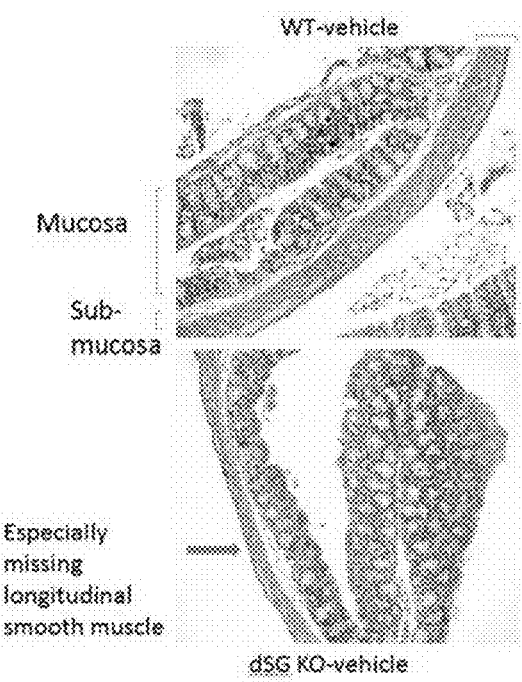
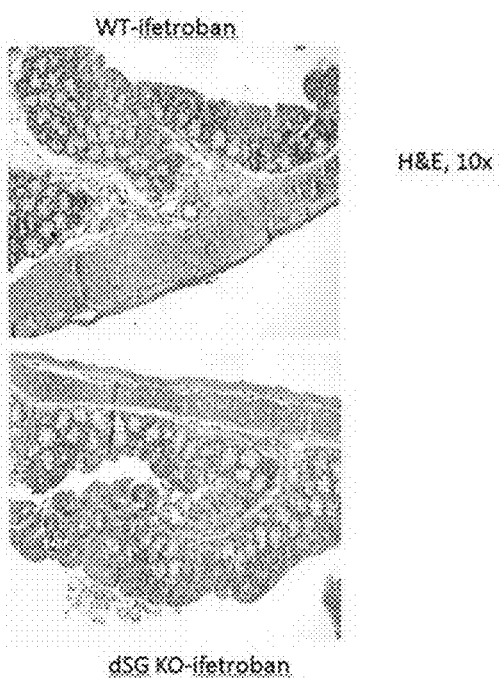
Fig. 13C  Fig. 13D

Fig. 14A
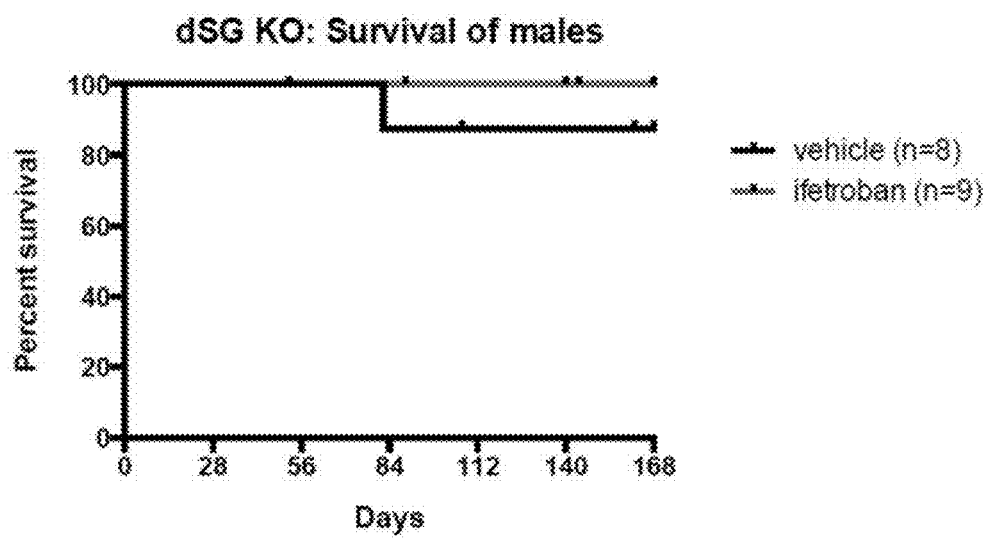
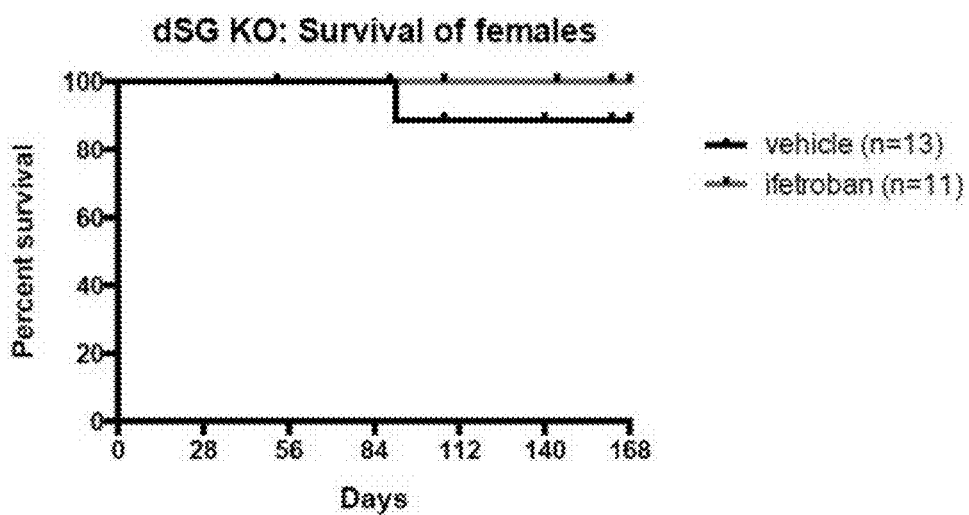
Fig. 14B

COMPOSITIONS AND METHODS OF TREATING MUSCULAR DYSTROPHY WITH THROMBOXANE-A₂ RECEPTOR ANTAGONISTS

This invention was made with government support under grant numbers R01HL095797 and P01HL08800 awarded by the National Institutes of Health. The government has certain rights in the invention.

FIELD OF THE INVENTION

The present invention is related to the use of thromboxane $A_2$ receptor antagonists (e.g., Ifetroban) in the treatment of muscular dystrophy in mammals, e.g., humans, and pharmaceutical compositions for the same comprising thromboxane $A_2$ receptor antagonists (e.g., Ifetroban) in an effective amount to treat these diseases.

BACKGROUND OF THE INVENTION

Muscular Dystrophy (MD) is a group of 30+ diseases that causes progressive weakness and loss of muscle mass due to mutations in dystrophin, a protein needed to form healthy muscle. Duchenne MD (DMD) comprises half of MD; affects 1 in 3,500 boys and ⅓ have no family history. Onset is between ages 2 and 3 and progresses rapidly. Becker MD (BMD) is the 2nd most common form of MD; 1 in 30,000 boys; BMD is milder and slowly progresses compared to DMD; symptoms may not be seen until teens, mid-20s or later. Limb-Girdle MD (LGMD) can affects as many as 1 in 14,500 and causes weakness and wasting of the muscles in the proximal arms and legs.

Complications of muscular dystrophy include inability to walk, breathing problems, scoliosis, cardiomyopathy and swallowing problems. There is no cure. Treatment to-date is to manage symptoms or slow progression.

Delta-sarcoglycan (DSG) is a transmembrane glycoprotein which forms as a complex, the dystrophin-associated glycoprotein complex (DGC). The DGC plays a central role in maintaining integrity of the cell membrane by linking the extracellular matrix ("ECM"; a substance containing collagen, elastin, proteoglycans, glycosaminoglycans, and fluid, produced by cells and in which the cells are embedded) and cytoskeleton (the inner structural elements, or backbone, of a cell. It consists of microtubules and various filaments that spread out through the cytoplasm, providing both structural support and a means of transport within the cell).

In both skeletal and cardiac muscle, the DGC consists of dystrophin, the syntrophins, a- and b-dystroglycan (a-, b-DG), the sarcoglycans (a-, b-, g-, d-SG), and sarcospan (SSPN).

Mutations in the dystrophin gene lead to high incidence of cardiomyopathy in DMD and BMD. Mutations in sarcoglycans within DGC are responsible for Limb-Girdle MD and associated with cardiomyopathy. A major function of dystrophin is to strengthen the sarcolemma by cross-linking the ECM with the cytoskeleton. Utrophin and a7b1 integrin fulfil the same function. Dystrophin works to connect sarcolemma to cytoplasmic actin cytoskeleton. Dysfunction produces membrane instability, elevated [Ca2+]I and disrupted NO signaling. γ- and δ-SG form a core necessary for delivery/retention of other SG to the membrane.

Patients with mutations in DSG (e.g., patients suffering from muscular dystrophy) present with cardiomyopathy.

Absence of dystrophin in Duchenne muscular dystrophy (DMD) causes progressive breakdown of muscle cells. In the heart, loss of dystrophin leads to abnormally increased intracellular calcium, degradation of contractile proteins, fibrosis, and myocardial death. With advances in respiratory support, cardiomyopathy is now a primary cause of death amongst DMD patients. DM D patients develop an insidious decline in cardiac function leading to heart failure and can also develop arrhythmias, with the potential for sudden cardiac death, even with minimal decrease in cardiac function by physical symptoms or echocardiography. Because of this, cardiac magnetic resonance (CMR) is useful for detection of early cardiac involvement in DMD patients. Increased myocardial fibrosis and expanded extracellular volume in CMR predicts left ventricular (LV) dysfunction, and are associated with an increased risk of arrhythmia and hospitalization for heart failure or death.

While less severely affected than skeletal and cardiac muscle, intestinal smooth muscle function can also be altered by atrophy and fibrosis. In DMD patients, particularly when wheelchair-bound, this can lead to poor gut motility, gastroesophageal reflux, and chronic constipation, which negatively affect patient quality of life. More critically, the possible complications of dilatation, fecal impaction, or intestinal pseudo-obstruction can be life-threatening.

The cellular damage characteristic of DMD is also associated with increased formation of reactive oxygen species, or oxidative stress. (Grosso, et al., Isoprostanes in dystrophinopathy: Evidence of increased oxidative stress. Brain Dev. 2008; 30(6):391-5. doi:10.1016/j.braindev.2007.11.005. PubMed PMID: 18180123). These free radicals can react with membrane phospholipids to form isoprostanes, which circulate freely after release by phospholipase, and the relatively stable 15-F2t-isoprostane (F2-IsoP) is a primary biomarker of in vivo oxidative stress. (Montuschi, et al., Isoprostanes: markers and mediators of oxidative stress. FASEB J. 2004; 18(15):1791-800. doi: 10.1096/fj.04-2330rev). Plasma F2-IsoP levels are increased in DMD patients (Grosso, et al., cited above), and urinary F2-IsoP levels are increased in heart failure patients, where they correlate with the severity of the disease (Cracowski, et al., Increased formation of F(2)-isoprostanes in patients with severe heart failure. Heart. 2000; 84(4):439-40. PubMed PMID:10995421; PMCID: PMC172944614). In addition to heralding cellular stress, isoprostanes can also be the source of damage via activation of the thromboxane/prostanoid receptor (TPr), and F2-IsoP signaling through the TPr decreases angiogenesis and causes vasoconstriction (Bauer, et al., Pathophysiology of isoprostanes in the cardiovascular system: implications of isoprostane-mediated thromboxane A2 receptor activation. Brit J Pharmacol. 2014; 171:3115-3115) and fibrosis (Acquaviva, et al. Signaling pathways involved in isoprostane-mediated fibrogenic effects in rat hepatic stellate cells. Free Radic Biol Med. 2013; 65:201-7, doi: 10.1016/j.freeradbiomed.2013.06.023. PubMed PMID: 23792773; Comporti, et al. Isoprostanes and hepatic fibrosis, Mol Aspects Med. 2008; 29(1-2):43-9. doi: 10.1016/j.mam.2007.09.011. PubMed PMID: 18061254).

Fibrosis is the formation of excess fibrous connective tissue in an organ or tissue in a reparative or reactive process. This can be a reactive, benign, or pathological state, and physiologically acts to deposit connective tissue, which can obliterate the architecture and function of the underlying organ or tissue. Fibrosis can be used to describe the pathological state of excess deposition of fibrous tissue, as well as the process of connective tissue deposition in healing. While the formation of fibrous tissue is normal, and fibrous tissue is a normal constituent of organs or tissues in the body, scarring caused by a fibrotic condition may obliterate the architecture of the underlying organ or tissue.

To date, there are no commercially available therapies that are effective in treating or preventing fibrotic disease. Conventional treatment frequently involves corticosteroids, such as prednisone, and/or other medications that help improve muscle strength and delay the progression of certain types of muscular dystrophy. Also, heart medications, such as angiotensin-converting enzyme (ACE) inhibitors or beta blockers may be administered to muscular dystrophy patients, if the muscular dystrophy damages the heart.

SUMMARY OF THE INVENTION

It is an object of the present invention to provide new methods of treating muscular dystrophy in mammals, e.g., humans.

In accordance with the above objects, the present invention provides for methods of treating muscular dystrophy by administering a therapeutically effective amount of a thromboxane $A_2$ receptor antagonist to a patient in need thereof.

In accordance with the above objects and others, the present invention is directed in part to a method of treating or ameliorating muscular dystrophy in a subject in need of treatment thereof, comprising administering a therapeutically effective amount of a thromboxane A2 receptor antagonist to the patient. The muscular dystrophy is fibrosis is selected from the group consisting of Duchenne MD (DMD), Becker MD, and Limb-Girdle MD. The thromboxane A2 receptor antagonist may be administered orally, intranasally, rectally, vaginally, sublingually, buccally, parenterally, or transdermally. In certain preferred embodiments, the method further comprises administering the thromboxane A2 antagonist to the patient on a chronic basis. In certain embodiments, the thromboxane $A_2$ receptor antagonist comprises a therapeutically effective amount of [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), and pharmaceutically acceptable salts thereof. In certain embodiments, the thromboxane $A_2$ receptor antagonist comprises a therapeutically effective amount of [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium). In certain preferred embodiments, the cardiac function of the patient is maintained or improved. Certain embodiments of the invention are directed to the method, wherein the thromboxane A2 receptor antagonist is administered prophylactically to prevent cardiomyopathy in the patient, and/or to prophylactically to prevent gastrointestinal dysfunction in the patient. In certain preferred embodiments, the therapeutically effective amount is from about 50 mg to about 500 mg. In certain preferred embodiments, the thromboxane A2 receptor antagonist is ifetroban and the therapeutically effective amount is from about 150 mg to about 350 mg per day. In certain embodiments, the ifetroban is administered orally. In certain embodiments, the present invention is directed to a method of treating and/or ameliorating muscular dystrophy in a patient in need thereof, comprising administering to a patient in need thereof a therapeutically effective amount of a thromboxane $A_2$ receptor antagonist to provide a desired plasma concentration of the thromboxane $A_2$ receptor antagonist of about 0.1 ng/ml to about 10,000 ng/ml.

The invention is also directed to a method of providing cardioprotective effects to a human patient(s) suffering from muscular dystrophy via the administration of a thromboxane $A_2$ receptor antagonist as described herein.

The invention is further directed to a method of improving right heart adaptation to load stress in a human patient(s) suffering from muscular dystrophy via the administration of a thromboxane $A_2$ receptor antagonist as described herein.

The invention is further directed to a method of treating cardiac and/or gastrointestinal dysfunction in a human patient suffering from muscular dystrophy, comprising chronically administering a therapeutically effective amount of a thromboxane A2 receptor antagonist to the human patient. In certain preferred embodiments, the thromboxane A2 receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), and pharmaceutically acceptable salts thereof, and in certain most preferred embodiments the thromboxane A2 receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium). The therapeutically effective amount may be, e.g., from about 100 mg to about 500 mg. The thromboxane A2 receptor antagonist may be administered, e.g., in an amount from about 50 or 100 mg to about 500 mg per day. In certain embodiments, the thromboxane A2 receptor antagonist is ifetroban or a pharmaceutically acceptable salt thereof and the daily dose is from about 150 mg to about 350 mg per day. In certain embodiments, the ifetroban is administered orally. In certain embodiments, the gastrointestinal dysfunction is smooth muscle dysfunction. In certain embodiments, the therapeutically effective amount of ifetroban provides improved ventricular function to the heart of the patient.

The present invention also relates to methods and compositions for treating muscular dystrophy in a mammal(s) or human(s) in need of treatment thereof, the method comprising administering a therapeutically effective amount of a thromboxane $A_2$ receptor antagonist to a subject(s) or patient(s) in need thereof. Preferably, the method of treatment comprises administering a composition comprising administering a therapeutically effective amount of a thromboxane $A_2$ receptor antagonist to a muscular dystrophy patient in need thereof in an amount effective to improve heart function. Further provided is a method of preventing fibrosis or sclerosis in a subject(s) or patient(s) in need of such treatment, comprising administering a composition comprising a thromboxane $A_2$ receptor antagonist in an amount effective to reduce the formation of fibrotic or sclerotic tissue that would occur in the absence of such treatment.

In a certain embodiment, the fibrosis is associated with a fibroproliferative disease selected from the group consisting of heart fibrosis, kidney fibrosis, liver fibrosis, lung fibrosis, and systemic sclerosis.

BRIEF DESCRIPTION OF THE DRAWINGS

The following drawings are illustrative of embodiments of the invention and are not meant to limit the scope of the invention as encompassed by the claims.

FIGS. 10A(dSG-Veh), 10B(dSG-veh), 10C(dSG-ifetroban) and 10D(dSG-ifetroban) show cardiac histology in dSG KO males (using Masson's trichrome, 2×). It can be seen that there is less fibrosis in the ifetroban treated RV. RV=right ventricle.

FIGS. 11A1, 11A2, 11A3 and 11A4 shows cardiac histology in dSG KO males (using Masson's trichrome, 10×) in the left ventricle (11A1=mouse #1, dSG KO-vehicle; 11A2=mouse #2, dSG KO-vehicle; 11A3=mouse #1, dSG KO-ifetroban; and 11A4=mouse #2, dSG KO-ifetroban); FIGS. 11B1, 11B2, 11B3 and 11B4 shows cardiac histology in the right ventricle (11B1=mouse #1, dSG KO-vehicle; 11B2=mouse #2, dSG KO-vehicle; 11B3=mouse #1, dSG KO-ifetroban; and 11B4=mouse #2, dSG KO-ifetroban). LV=left ventricle; RV=right ventricle. Less fibrosis was seen in ifetroban-treated KO mice.

FIGS. 12A(WT1), 12B(dSG-KO-vehicle), 12C(WT2) and 12D(dSG-KO-ifetroban) shows skeletal muscle histology in WT and dSG KO males (tibialis cross-section, using Masson's trichrome). Some fibrosis may be due to specific section of muscle.

FIGS. 13A(WT-vehicle), 13B(WT-ifetroban), 13C(dSG KO-vehicle) and 13D(dSG-KO-ifetroban) are cross-sections of intestinal tissue showing that ifetroban may prevent the loss of intestinal smooth muscle in the large intestine Muscularis. The DSG KO mice were missing smooth muscle (especially missing longitudinal smooth muscle) while ifetroban-treated mice have similar sections to WT smooth muscle. "H&E"=Hematoxylin & eosin. FIG. 13 shows that ifetroban-treated dSG KO mice have less fibrosis than vehicle-treated dSG KO mice.

FIGS. 14A and 14B are graphs showing the percent survival of dSG KO males (14A) and dSG females (14B) treated with ifetroban or vehicle.

DETAILED DESCRIPTION OF THE INVENTION

Figure 1A:
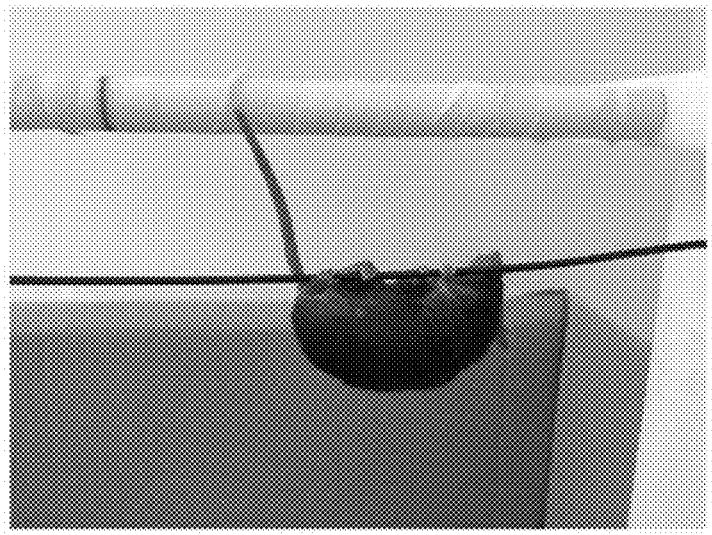
FIG. 1A is a photograph of a vehicle-treated DKO (double knockout) Mouse at 10 weeks.

In accordance with the above stated objects, it is believed that administration of a therapeutically effective amount of a thromboxane $A_2$ receptor antagonist to a subject(s) or patient(s) in need thereof can treat cardiomyopathy associated with muscular dystrophy.

The phrase "therapeutically effective amount" refers to that amount of a substance that produces some desired local or systemic effect at a reasonable benefit/risk ratio applicable to any treatment. The effective amount of such substance will vary depending upon the subject and disease condition being treated, the weight and age of the subject, the severity of the disease condition, the manner of administration and the like, which can readily be determined by one of ordinary skill in the art.

The TPr is a G protein-coupled receptor which is located in platelets, immune cells, smooth muscle, and cardiomyocytes, and its activation has deleterious consequences in the heart. We have recently shown (in our U.S. Patent Application Publication No. 2015/0328190) that blockade of the TPr with the antagonist ifetroban dramatically decreases right ventricular fibrosis and improves cardiac function in a pressure-overload model of pulmonary arterial hypertension. Although the TPr has multiple endogenous ligands including F2-IsoP, thromboxane A2, prostaglandin H2, and 20-HETE, blockade of thromboxane synthase with ozagrel or prostaglandin/thromboxane synthesis with aspirin had no effect on fibrosis or cardiac function in our pressure-overload model. Thus, F2-IsoP is an excellent candidate as an activating ligand of the TPr in the stressed heart. Beyond the right ventricle, TPr activation also contributes to LV hypertrophy and heart failure in mouse models of systemic hypertension and Gh-overexpression. In addition, TPr activation causes increased intracellular calcium, arrhythmia, and cell death in ventricular cardiomyocytes, and decreased peristalsis in the gut. Although the role of the TPr in MD is unknown, these actions position the receptor to have an impact on some of the most pressing concerns in DMD.

Applicants explored the possibility that TPr activity may contribute to pathology in muscular dystrophy. In preliminary studies, the effects of blocking TPr activity in a δ-sarcoglycan knockout (dSG KO) mouse model of limb-girdle muscular dystrophy (LGMD). We found that treatment with the antagonist ifetroban, given in drinking water, limits the formation of cardiac fibrosis and prevents a decline in cardiac function while normalizing elevated plasma cardiac troponin I levels, a clinically-used biomarker for cardiac injury. The inhibition of LV epicardial fibrosis may have particular applicability to DMD patients, where cardiac fibrosis typically begins in the sub-epicardium of the left ventricular (LV) free wall and progresses to include the remaining LV free wall and septum. Ifetroban treatment also significantly improved survival in dSG KO mice, and in utrophin/dystrophin double knockout (DKO) mice, a model of severe DMD, TPr antagonism with ifetroban improved 10-week survival from 56% to 100%. Therefore, it is believed that TPr activity contributes to pathology in muscular dystrophy.

In accordance with the present invention, it is believed that increased isoprostane signaling through the TPr contributes to cardiomyopathy and smooth muscle dysfunction in DMD, and thus treatment with ifetroban, an orally active TPr antagonist, will improve cardiac and gut function and decrease spontaneous mortality in mammals (as demonstrated in preclinical mouse models of DMD). It is also believed that treatment with a thromboxane A₂ receptor antagonist (ifetroban) may contribute to cardioprotection by increasing the regenerative capability of the heart, and therefore may provide functional improvement of the heart (e.g., improved ventricular function). Thus, the invention is directed in part to the use of TPr antagonists as a treatment for cardiac and/or gastrointestinal dysfunction in DMD. The invention is also directed in part to the use of TPR antagonists for providing cardioprotection by increasing the regenerative capability of the heart and/or providing functional improvement of the heart of a muscular dystrophy (human) patient.

The term "thromboxane A2 receptor antagonist" as used herein refers to a compound that inhibits the expression or activity of a thromboxane receptor by at least or at least about 30%, 35%, 40%, 45%, 50%, 55%, 60%, 65%, 70%, 75%, 80%, 85%, 90%, 95%, 96%, 97%, 98%, 99%, or 100% in a standard bioassay or in vivo or when used in a therapeutically effective dose. In certain embodiments, a thromboxane A2 receptor antagonist inhibits binding of thromboxane A₂ to the receptor. Thromboxane A2 receptor antagonists include competitive antagonists (i.e., antagonists that compete with an agonist for the receptor) and non-competitive antagonists. Thromboxane A2 receptor antagonists include antibodies to the receptor. The antibodies may be monoclonal. They may be human or humanized antibodies. Thromboxane A2 receptor antagonists also include thromboxane synthase inhibitors, as well as compounds that have both thromboxane A2 receptor antagonist activity and thromboxane synthase inhibitor activity.

Thromboxane A₂ Receptor Antagonist

The discovery and development of thromboxane A₂ receptor antagonists has been an objective of many pharmaceutical companies for approximately 30 years (see, Dogne J-M, et al., Exp. Opin. Ther. Patents 11: 1663-1675 (2001)). Certain individual compounds identified by these companies, either with or without concomitant thromboxane A₂ synthase inhibitory activity, include ifetroban (BMS), ridogrel (Janssen), terbogrel (BI), UK-147535 (Pfizer), GR 32191 (Glaxo), and S-18886 (Servier). Preclinical pharmacology has established that this class of compounds has effective antithrombotic activity obtained by inhibition of the thromboxane pathway. These compounds also prevent vasoconstriction induced by thromboxane A₂ and other prostanoids that act on the thromboxane A₂ receptor within the vascular bed, and thus may be beneficial for use in preventing and/or treating hepatorenal syndrome and/or hepatic encephalopathy.

Suitable thromboxane A2 receptor antagonists for use in the present invention may include, for example, but are not limited to small molecules such as ifetroban (BMS; [1 S-(1α,2α,3α,4α)]-2-[[3-[4-[(pentylamino)carbony-1]-2-oxazolyl]-7-oxabicyclo[2.2.1]hept-2 yl]methyl]benzenepropanoic acid), as well as others described in U.S. Patent Application Publication No. 2009/0012115, the disclosure of which is hereby incorporated by reference in its entirety.

Additional thromboxane A2 receptor antagonists suitable for use herein are also described in U.S. Pat. No. 4,839,384 (Ogletree); U.S. Pat. No. 5,066,480 (Ogletree, et al.); U.S. Pat. No. 5,100,889 (Misra, et al.); U.S. Pat. No. 5,312,818 (Rubin, et al.); U.S. Pat. No. 5,399,725 (Poss, et al.); and U.S. Pat. No. 6,509,348 (Ogletree), the disclosures of which are hereby incorporated by reference in their entireties. These may include, but are not limited to, interphenylene 7-oxabicyclo-heptyl substituted heterocyclic amide prostaglandin analogs as disclosed in U.S. Pat. No. 5,100,889, including:

[1S-(1α,2α,3α,4α)]-2-[[3-[4-[[(4-cyclohexylbutyl)amino]carbonyl]-2-oxazolyl]-7-oxabicyclo[2.2.1]-hept-2-yl]methyl]benzenepropanoic acid (SQ 33,961), or esters or salts thereof;

[1S-(1α,2α,3α,4α)]-2-[[3-[4-[[[(4-chlorophenyl)-butyl]amino]carbonyl]-2-oxazolyl]-7-oxabicyclo[2.2.1]hept-2-yl]methyl]benzenepropanoic acid or esters, or salts thereof;

[1S-(1α,2α,3α,4α)]-3-[[3-[4-[[(4-cyclohexylbutyl)-amino]carbonyl]-2-oxazolyl]-7-oxabicyclo]2.2.1]hept-2-yl]benzene acetic acid, or esters or salts thereof;

[1S-(1α,2α,3α,4α)]-[2-[[3-[4-[[(4-cyclohexylbutyl)amino]carbonyl]-2-oxazolyl]-7-oxabicyclo[2.2.1]hept-2-yl]methyl]phenoxy]acetic acid, or esters or salts thereof;

[1S-(1α,2α,3α,4α]-2-[[3-[4-[[(7,7-dimethyloctyl)-amino]carbonyl]-2-oxazolyl]-7-oxabicyclo[2.2.1]hept-2-yl]-methyl]benzenepropanoic acid, or esters or salts thereof.

7-oxabicycloheptyl substituted heterocyclic amide prostaglandin analogs as disclosed in U.S. Pat. No. 5,100,889, issued Mar. 31, 1992, including [1S-[1α,2α(Z),3α,4α)]-6-[3-[4-[[(4-cyclohexylbutyl)amino]-carbonyl]-2-oxazolyl]-7-oxabicyclo[2.2.1]hept-2-yl]-4-hexenoic acid, or esters or salts thereof;

[1 S-[1α,2α(Z),3α,4α)]]-6-[3-[4-[[(4-cyclohexylbutyl)amino]carbonyl]-2-thiazolyl]-7-oxabicyclo[2.2.1]hept-2-yl]-4-hexenoic acid, or esters or salts thereof;

[1S-[1α,2α (7),3α,4α)]]-6-[3-[4-[[(4-cyclohexyl-buty)methylamino]carbonyl]-2-oxazolyl]-7-oxabicyclo-[2.2.1]hept-2-yl]-4-hexenoic acid, or esters or salts thereof;

[1S-[1α,2α(Z),3α,4α)]]-6-[3-[4-[(1-pyrrolidinyl)-carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-(cyclohexylamino)-carbonyl]-2-oxazolyl]-7-oxabicyclo[2.2.1]hept-2-yl-4-hexenoic acid or esters or salts thereof;

[1S-[1α,2α(Z),3α,4α)]]-6-[3-[4-[[(2-cyclohexyl-ethyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[[2-(4-chiorophenyl)ethyl]amino]carbonyl]-2-oxazolyl]-7-oxabicyclo-[2.2.1]hept-2-yl]-4-hexenoic acid, or esters or salts thereof,

[1S-[1α,2α(Z),3α,4α)]]-6-[3-[4-[[(4-chlorophenyl)-amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[[4-(4-chloro-phenyl)butyl]amino]carbonyl]-2-oxazolyl]-7-oxabicyclo-[2.2.1]hept-2-yl]-4-hexenoic acid, or esters or salts thereof,

[1S-[11α,2α(Z),3α,4α)]]-6-[3-[4.alpha.-[[-(6-cyclohexyl-hexyl)amino]carbonyl]-2-oxazolyl]-7-oxabicyclo[2.2.1]hept-2-yl]-4-hexenoic acid, or esters, or salts thereof,

[1S-[1α,2α(Z),3α,4α)]]-6-[3-[4-[[(6-cyclohexyl-hexyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[(propylamino)-carbonyl]-2-oxazolyl]-7-oxabicyclo[2.2. I]hept-2-yl]-4-hexenoic acid, or esters or salts thereof

[1S-[1α,2α(Z),3α,4α)]]-6-[3-[4-[[(4-butylphenyl)-amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[(2,3-dihydro-1H-indol-1-yl)carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[(4-cyclohexyl-butyl)amino]carbonyl]-2-oxazolyl]-7-oxabicyclo[2.2.1]hept-2-yl]-N-(phenylsulfonyl)-4-hexenamide;

[1S-[1α,2α(Z),3α,4α)]]-6-[3-[4-[[(4-cyclohexyl-butyl)amino]carbonyl]-2-oxazolyl]-N-(methylsulfonyl)-7-oxabicyclo[2.2.1]hept-2-yl]-4-hexenamide;

[1S-[1α,2α(Z),3α,4α)]]-7-[3-[4-[[(4-cyclohexyl-butyl)amino]carbonyl]-2-oxazolyl]-7-oxabicyclo (2.2.1)hept-2-yl]-5-heptenoic acid, or esters or salts thereof;

[1S-[1α,2α(Z),3α,4α)]]-6-[3-[4-[[(4-cyclohexyl-butyl)amino]carbonyl]-1H-imidazol-2-yl]-7-oxabicyclo-[2.2.1]hept-2-yl]-4-hexenoic acid or esters or salts thereof:

[1S-[1α, 2α,3α,4α)]]-6-[3-[4-[[(7,7-dimethyloctyl)-amino]carbonyl]-2-oxazolyl]-7-oxabicyclo[2.2.1]hept-2-yl]-4-hexenoic acid, or esters or salts thereof;

[1S-[1α,2α(E),3α,4α)]]-6-[3-[4-[[(4-cyclohexyl-butyl)amino]carbonyl]-2-oxazolyl]-7-oxabicyclo[22.2.]hept-2-yl]-4-hexenoic acid;

[1S-[1α,2α,3α,4α)]]-3-[4-[[(4-(cyclohexylbutyl)-amino]carbonyl]-2-oxazolyl]-7-oxabicyclo[2.2.1]heptane-2-hexanoic acid or esters or salts thereof,

[1S-[1α,2α(Z),3α,4α)]-6-[3-[4-[[(4-cyclohexyl-butyl)amino]carbonyl]-2-oxazolyl]-7-oxabicyclo-[2.2.1]hept-2-yl]-4-hexenoic acid, or esters or salts thereof;

7-oxabicycloheptane and 7-oxabicycloheptene compounds disclosed in U.S. Pat. No. 4,537,981 to Snitman et al, the disclosure of which is hereby incorporated by reference in its entirety, such as [1S-(1α,2α(Z),3α(1E,3S*, 4R*), 4α)]]-7-[3-(3-hydroxy-4-phenyl-1-pentenyl)-7-oxabicyclo[2.2.1]hept-2-yl]-5-heptenoic acid (SQ 29,548); the 7-oxabicycloheptane substituted aminoprostaglandin analogs disclosed in U.S. Pat. No. 4,416,896 to Nakane et al, the disclosure of which is hereby incorporated by reference in its entirety, such as [1 S-[1α,2α(Z),3α,4α)]]-7-[3-[[2-(phenylamino)carbonyl]-hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, the disclosure of which is hereby incorporated by reference in its entirety, such as, [1S-[1α, 2α(Z),3α,4α)]]-7-[3-[[[[(1-oxoheptyl)amino]-acetyl]amino]methyl]-7-oxabicyclo[2.2.1]hept-2-yl]-5-heptenoic acid and the corresponding tetrazole, and [1S-[1α,2α(Z),3α,4α)]]-7-[3-[[[[(4-cyclohexyl-1-oxobutyl)-amino]acetyl]amino]methyl]-7-oxabicyclo[2.2.1]hept-2-yl]-5-heptenoic acid;

7-oxabicycloheptane imidazole prostaglandin analogs as disclosed in U.S. Pat. No. 4,977,174, the disclosure of which is hereby incorporated by reference in its entirety, such as [S-[1α,2α(Z),3α,4α)]]-6-[3-[[4-(4-cyclohexyl-I-hydroxybutyl)-1H-imidazole-1-yl]methyl]-7-oxabicyclo[2.2.1]hept-2-yl]-4-hexenoic acid or its methyl ester;

[1S-[1α,2α(Z),3α,4α)]]-6-[3-[[4-(3-cyclohexyl-propyl)-1H-imidazol-1-yl]methyl]-7-oxabicyclo[2.2.1]hept-2-yl]-4-hexenoic acid or its methyl ester;

[1S-[1α,2α(X(Z),3α,4α)]]-6-[3-[[4-(4-cyclohexyl-1-oxobutyl)-H-imidazol-1-yl]methyl]-7-oxabicyclo[2.2.1]hept-2-yl]-4-hexenoic acid or its methyl ester;

[1S-[1α,2α(Z),3α,4α]]-6-[3-(1H-imidazol-1-ylmethyl)-7-oxabicyclo[2.2.1]hept-2-yl]-4-hexenoic acid or its methyl ester; or

[1S-[1α,2α(Z),3α,4α)]]-6-[3-[[4-[[(4-cyclohexyl-butyl)amino]carbonyl]-1H-imidazol-1-yl]methyl-7-oxabicyclo-[2.2.1]-hept-2-yl]-4-hexenoic acid, or its methyl ester;

The phenoxyalkyl carboxylic acids disclosed in U.S. Pat. No. 4,258,058 to Witte et al, the disclosure of which is hereby incorporated by reference in its entirety, including 4-[2-(benzenesulfamido)ethyl]phenoxy-acetic acid (BM 13,177-Boehringer Mannheim), the sulphonamidophenyl carboxylic acids disclosed in U.S. Pat. No. 4,443,477 to Witte et al, the disclosure of which is hereby incorporated by reference in its entirety, including 4-[2-(4-chlorobenzene-sulfonamido)ethyl]-phenylacetic acid (BM 13,505, Boehringer Mannheim), the arylthioalkylphenyl carboxylic acids disclosed in U.S. Pat. No. 4,752,616, the disclosure of which is hereby incorporated by reference in its entirety, including 4-(3-((4-chlorophenyl)sulfonyl)propyl)benzene acetic acid.

Other examples of thromboxane $A_2$ receptor antagonists suitable for use herein include, but are not limited to vapiprost (which is a preferred example), (E)-5-[[[(pyridinyl)]3-(trifluoromethyl)phenyl]methylene]amino]l-oxy] pentanoic acid also referred to as R68,070-Janssen Research Laboratories, 3-[1-(4-chlorophenylmethyl)-5-fluoro-3-methylindol-2-yl]-2,-2-dimethylpropanoic acid [(L-655240 Merck-Frosst) Eur. J. Pharmacol. 135(2):193, March 17, 87], 5(Z)-7-([2,4,5-cis]-4-(2-hydroxyphenyl)-2-trifluoromethyl-1,3-dioxan-5-yl)heptenoic acid (ICI 185282, Brit. J. Pharmacol. 90 (Proc. Suppl):228 P-Abs, March 87), 5(Z)-7-[2,2-dimethyl-4-phenyl-1,3-dioxan-cis-5-yl]heptenoic acid (ICI 159995, Brit. J. Pharmacol. 86 (Proc. Suppl):808 P-Abs., December 85), N,N'-bis[7-(3-chlorobenzeneamino-sunfony-1)-1,2,3,4-tetrahydro-isoquinolyl]disulfonylimide (SKF 88046, Pharmacologist 25(3):116 Abs., 117 Abs, August 83), (1.alpha.(Z)-2.beta., 5.alpha.]-(+)-7-[5-[[(1,1'-biphenyl)-4-yl]-methoxy]-2-(4-morpholinyl)-3-oxocyclopentyl]-4-heptenoic acid (AH 23848-Glaxo, Circulation 72(6):1208, December 85, levallorphan allyl bromide (CM 32,191 Sanofi, Life Sci. 31 (20-21):2261, November 15,82), (Z,2-endo-3-oxo)-7-(3-acetyl-2-bicyclo[2.2.1]heptyl-5-hepta-3Z-enoic acid, 4-phenyl-thiosemicarbazone (EP092-Univ. Edinburgh, Brit. J. Pharmacol. 84(3):595, March 85); GR 32,191 (Vapiprost)-[1R-[1.alpha.(Z), 2.beta., 3.beta., 5.alpha.]]-(+)-7-[5-([1,1'-biphenyl]-4-ylmethoxy)-3-hydroxy-2-(1-piperidinyl)cyclopentyl]-4-heptenoic acid; ICI 192,605-4(Z)-6-[(2,4,5-cis)2-(2-chlorophenyl)-4-(2-hydroxyphenyl)-1,3-dioxan-5-yl]hexenoic acid; BAY u 3405 (ramatroban)-3-[[(4-fluorophenyl)-sulfonyl]amino]-1,2,3,4-tetrahydro-9H-c-arbazole-9-propanoic acid; or ONO 3708-7-[2.alpha., 4.alpha.-(dimethylmethano)-6.beta.-(2-cyclopentyl-2.beta.-hydroxyacetami-do)-1.alpha.-cyclohexyl]-5 (Z)-heptenoic acid; (.+-.)(5Z)-7-[3-endo-((phenylsulfonyl)amino]-bicyclo[2.2.1]hept-2-exo-yl]-heptenoic acid (S-1452, Shionogi domitroban, Anboxan®); (−)6,8-difluoro-9-p-methylsulfonylbenzyl-1,2,3,4-tetrahydrocarbazol-1-yl-acetic acid (L670596. Merck) and (3-[1-(4-chlorobenzyl)-5-fluoro-3-methyl-indol-2-yl]-2,2-dimethylpropanoic acid (L655240, Merck).

The preferred thromboxane A2 receptor antagonist of the present invention is ifetroban or any pharmaceutically acceptable salts thereof.

In certain preferred embodiments the preferred thromboxane A2 receptor antagonist is ifetroban sodium (known chemically as [1S-(1α,2α,3α,4α)]-2-[[3-[4-[(Pentylamino)carbonyl]-2-oxazolyl]-7-oxabicyclo[2.2. L]hept-2-yl]methyl]-benzenepropanoic acid, monosodium salt.

Methods of Treatment

In certain embodiments of the present invention there is provided a method of treating and/or ameliorating cardiomyopathies in a patient or patient population by administration of a therapeutically effective amount of a thromboxane $A_2$ receptor antagonist to a patient(s) in need thereof.

The administration of a therapeutically effective amount of a thromboxane $A_2$ receptor antagonist may be accomplished via any therapeutically useful route of administration, including but not limited to orally, intranasally, rectally, vaginally, sublingually, buccally, parenterally, or transdermally. In certain preferred embodiments, the thromboxane $A_2$ receptor antagonist is administered parenterally. In certain further embodiments, the thromboxane $A_2$ receptor antagonist is administered by intra-articular injection. In certain further embodiments, the thromboxane $A_2$ receptor antagonist is administered directly to the affected anatomic site. In another embodiment, the thromboxane $A_2$ receptor antagonist is administered through the hepatic artery.

In certain preferred embodiments, the plasma concentrations of thromboxane $A_2$ receptor antagonists range from about 0.1 ng/ml to about 10,000 ng/ml. Preferably, the plasma concentration of thromboxane $A_2$ receptor antagonists range from about 1 ng/ml to about 1,000 ng/ml.

When the thromboxane $A_2$ receptor antagonists is ifetroban, the desired plasma concentration for treatment of cardiomyopathies in muscular dystrophies in certain embodiments should be greater than about 10 ng/mL (ifetroban free acid). Some therapeutic effects of thromboxane $A_2$ receptor antagonist, e.g., ifetroban, may be seen at concentrations of greater than about 1 ng/mL.

The dose administered should be adjusted according to age, weight and condition of the patient, as well as the route of administration, dosage form and regimen and the desired result.

In order to obtain the desired plasma concentration of thromboxane $A_2$ receptor antagonists for the treatment of cardiomyopathy in muscular dystrophy patients, daily doses of the thromboxane $A_2$ receptor antagonists preferably range from about 0.1 mg to about 5000 mg. In certain preferred embodiments, the thromboxane $A_2$ receptor antagonist is administered on a chronic basis. Daily doses may range from about 1 mg to about 1000 mg; about 10 mg to about 1000 mg; about 50 mg to about 500 mg; about 100 mg to about 500 mg; about 200 mg to about 500 mg; about 300 mg to about 500 mg; or from about 400 mg to about 500 mg per day. In certain preferred embodiments where the mammal is a human patient, the therapeutically effective amount is from about 100 mg to about 2000 mg per day, or from about 10 mg or about 100 mg to about 1000 mg per day, and certain embodiments more preferably from about 50 to about 500 mg per day, or from about 100 mg to about 500 mg per day. The daily dose may be administered in divided doses or in one bolus or unit dose or in multiple dosages administered concurrently. In this regard, the ifetroban may be administered orally, intranasally, rectally, vaginally, sublingually, buccally, parenterally, or transdermally. In certain preferred embodiments, the pharmaceutical composition described above, the therapeutically effective amount is from about 10 mg to about 1000 mg ifetroban (or pharmaceutically acceptable salt thereof) per day. In certain preferred embodiments, the therapeutically effective amount is from about 100 to about 500 mg per day, and in certain embodiments from about 150 mg to about 350 mg per day will produce therapeutically effective plasma levels of ifetroban free acid for the treatment of muscular dystrophy. In certain preferred embodiments, a daily dose of ifetroban sodium from about 10 mg to about 250 mg (ifetroban free acid amounts) will produce therapeutically effective plasma levels of ifetroban free acid for the treatment of muscular dystrophy.

Preferably, the therapeutically effective plasma concentration of thromboxane $A_2$ receptor antagonists ranges from about 1 ng/ml to about 1,000 ng/ml for the treatment of muscular dystrophy.

When the thromboxane $A_2$ receptor antagonist is ifetroban, the desired plasma concentration for providing an inhibitory effect of $A_2$/prostaglandin endoperoxide receptor (TPr) activation, and thus a reduction of cerebral microvascular activation should be greater than about 10 ng/mL (ifetroban free acid). Some inhibitory effects of thromboxane $A_2$ receptor antagonist, e.g., ifetroban, may be seen at concentrations of greater than about 1 ng/mL.

The dose administered must be carefully adjusted according to age, weight and condition of the patient, as well as the route of administration, dosage form and regimen and the desired result.

However, in order to obtain the desired plasma concentration of thromboxane $A_2$ receptor antagonists, daily doses of the thromboxane $A_2$ receptor antagonists ranging from about 0.1 mg to about 5000 mg should be administered. Preferably, the daily dose of thromboxane $A_2$ receptor antagonists ranges from about 1 mg to about 1000 mg; about 10 mg to about 1000 mg; about 50 mg to about 500 mg; about 100 mg to about 500 mg; about 200 mg to about 500 mg; about 300 mg to about 500 mg, and about 400 mg to about 500 mg per day.

In certain preferred embodiments, a daily dose of ifetroban sodium from about 10 mg to about 250 mg (ifetroban free acid amounts) will produce effective plasma levels of ifetroban free acid.

Pharmaceutical Compositions

The thromboxane $A_2$ receptor antagonists of the present invention may be administered by any pharmaceutically effective route. For example, the thromboxane $A_2$ receptor antagonists may be formulated in a manner such that they can be administered orally, intranasally, rectally, vaginally, sublingually, buccally, parenterally, or transdermally, and, thus, be formulated accordingly.

In certain embodiments, the thromboxane $A_2$ receptor antagonists may be formulated in a pharmaceutically acceptable oral dosage form. Oral dosage forms may include, but are not limited to, oral solid dosage forms and oral liquid dosage forms.

Oral solid dosage forms may include, but are not limited to, tablets, capsules, caplets, powders, pellets, multiparticulates, beads, spheres and any combinations thereof. These oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

Depending on the desired release profile, the oral solid dosage forms of the present invention may contain a suitable amount of controlled-release agents, extended-release agents, modified-release agents.

Oral liquid dosage forms include, but are not limited to, solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol and combinations thereof.

In certain embodiments of the present invention, the thromboxane $A_2$ receptor antagonists may be formulated into a dosage form suitable for parenteral use. For example, the dosage form may be a lyophilized powder, a solution, suspension (e.g., depot suspension).

In other embodiments, the thromboxane $A_2$ receptor antagonists may be formulated into a topical dosage form such as, but not limited to, a patch, a gel, a paste, a cream, an emulsion, liniment, balm, lotion, and ointment.

DETAILED DESCRIPTION OF THE PREFERRED EMBODIMENTS

The following examples are not meant to be limiting and represent certain embodiments of the present invention.

Example I

In this example, ifetroban sodium tablets are prepared with the following ingredients listed in Table 1:

TABLE 1

| Ingredients | Percent by weight |
| --- | --- |
| Na salt of Ifetroban | 35 |
| Mannitol | 50 |
| Microcrystalline Cellulose | 8 |
| Crospovidone | 3.0 |
| Magnesium Oxide | 2.0 |
| Magnesium Stearate | 1.5 |
| Colloidal Silica | 0.3 |

The sodium salt of ifetroban, magnesium oxide, mannitol, microcrystalline cellulose, and crospovidone is mixed together for about 2 to about 10 minutes employing a suitable mixer. The resulting mixture is passed through a #12 to #40 mesh size screen. Thereafter, magnesium stearate and colloidal silica are added and mixing is continued for about 1 to about 3 minutes.

The resulting homogeneous mixture is then compressed into tablets each containing 35 mg, ifetroban sodium salt.

Example II

In this example, 1000 tablets each containing 400 mg of ifetroban sodium are produced from the following ingredients listed in Table 2:

TABLE 2

| Ingredients | Amount |
| --- | --- |
| Na salt of Ifetroban | 400 gm |
| Corn Starch | 50 g |
| Gelatin | 7.5 g |
| Microcrystalline Cellulose (Avicel) | 25 g |
| Magnesium Stearate | 2.5 g |

Example III

An injectable solution of ifetroban sodium is prepared for intravenous use with the following ingredients listed in Table 3:

TABLE 3

| Ingredients | Amount |
| --- | --- |
| Ifetroban Sodium | 2500 mg |
| Methyl Paraben | 5 mg |
| Propyl Paraben | 1 mg |
| Sodium Chloride | 25,000 mg |
| Water for injection q.s. | 5 liter |

The sodium salt of ifetroban, preservatives and sodium chloride are dissolved in 3 liters of water for injection and then the volume is brought up to S liters. The solution is filtered through a sterile filter and aseptically filled into pre-sterilized vials which are then closed with pre-sterilized rubber closures. Each vial contains a concentration of 75 mg of active ingredient per 150 ml of solution.

Example IV dSG KO mice, chosen for their cardiac phenotype, are a model of LGMD, but DMD which occurs in approximately 1:3500 male births (1), is liar more common a disease than LGMD. The mdx mouse model of DMD poorly replicates the shortened life expectancy, cardiac fibrosis, and cardiomyopathy seen in DMD patients. The utrophin/dystrophin DKO model had significant mortality by 10 weeks, although treatment with the TPr antagonist ifetroban led to 100% survival to this predetermined timepoint. Although TPr antagonism may prevent spontaneous death in DMD, due to severe kyphosis and frailty we were not able to obtain much useful cardiac data with the DKO model of DMD.

Example 4 utilized West/Carrier Muscular Dystrophy Animal Models (Delta-sarcoglycan knock-out mice (sgcd−/−)). Mice devoid of DSG develop cardiomyopathy and MD with signs of progressive disease such as necrosis, muscular regeneration, inflammation and fibrosis within the first 3 months of life. Mice that are homozygous for the targeted mutation are viable, fertile and normal in size. No gene product (protein) is immunodetected in skeletal muscle microsomal preparations. At 8 weeks of age there is an onset of sudden mortality, with a 50% survival rate at 28 weeks. Elevated creatine kinase serum levels are indicative of striated muscle degeneration. Histopathology of skeletal muscle tissue reveals degeneration and regeneration of muscle fibers, inflammatory infiltrate, perivascular fibrosis and calcification. At 12 weeks of age, cardiac muscle tissue also begins to show degeneration, inflammatory infiltration and perivascular fibrosis. Myofiber membranes have permeability defects as assessed by Evans blue dye uptake into myofiber cytoplasm. Skeletal muscle of mutant mice have an enhanced sensitivity to mechanically induced sarcolemmal damage. Dystrophin deficient mice have minimal clinical symptoms with lifespan reduced by only 25% unlike humans with DMD reduced by 75%, possibly due to compensatory mechanisms upregulated in mice. A major function of dystrophin is to strengthen the sarcolemma by cross-linking the ECM with the cytoskeleton. Utrophin and a7b integrin fulfil the same function and are upregulated in mdx mice. They work to connect sarcolemma to cytoplasmic actin cytoskeleton. Dysfunction produces membrane instability, elevated [$Ca^{2+}$]I and disrupted NO signaling. γ- and δ-SG form a core necessary for delivery/retention of other SG to the membrane.

While the DSG KO (sgcd−/−) mice lack functional delta-sarcoglycan, the MD phenotype is milder than the human disease. Since utrophin, a dystrophin-related protein, is able to compensate for the loss of dystrophin, loss of utrophin and dystrophin (DKO) results in a more severe phenotype. DKO are significantly smaller and show more severe muscle disease (similar or worse than that of humans with MD). The mice are difficult to generate and care for, and often die prematurely. Ifetroban treatment was started at 3 weeks upon weaning.

In Example IV, vehicle-treated mice were carefully cared for to get them to reach 10 weeks of life (e.g., the mice were checked on them constantly and a low dish of crushed food and water was placed right next to where the mice huddled in the cage, in an attempt to get them some nutrition without them needing to move much).

Figure 1B:
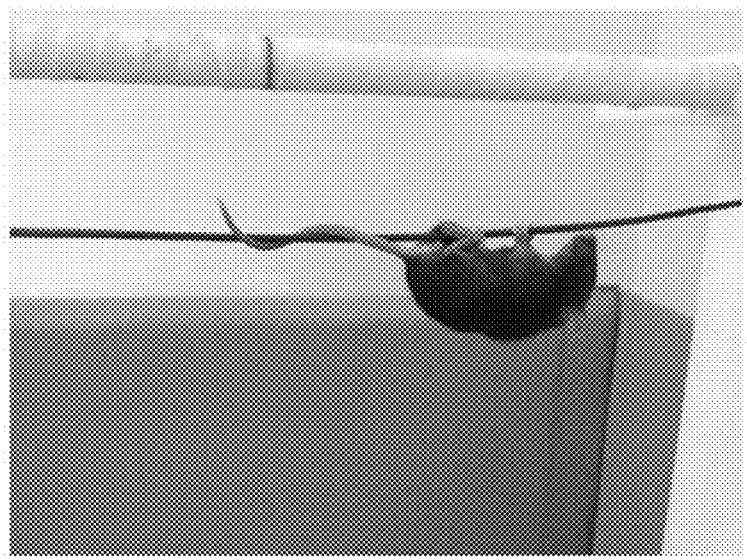
FIG. 1B is a photograph of an ifetroban-treated DKO mouse at 10 weeks.

FIG. 1 are photos of a vehicle-treated compared with an ifetroban-treated DKO mouse. FIG. 1A is a photograph of a vehicle-treated DKO Mouse at 10 weeks. FIG. 1B is a photograph of an ifetroban-treated DKO mouse at 10 weeks. The ability to wrap the tail around the wire is dependent on muscle function. A reason the DKO mice are really hard to evaluate in the wire hang is that they have such severe scoliosis that their hind paws are very close to their front paws, so raising their hind paws to get a 4-limbed grip is not difficult despite their affliction.

Figure 2:
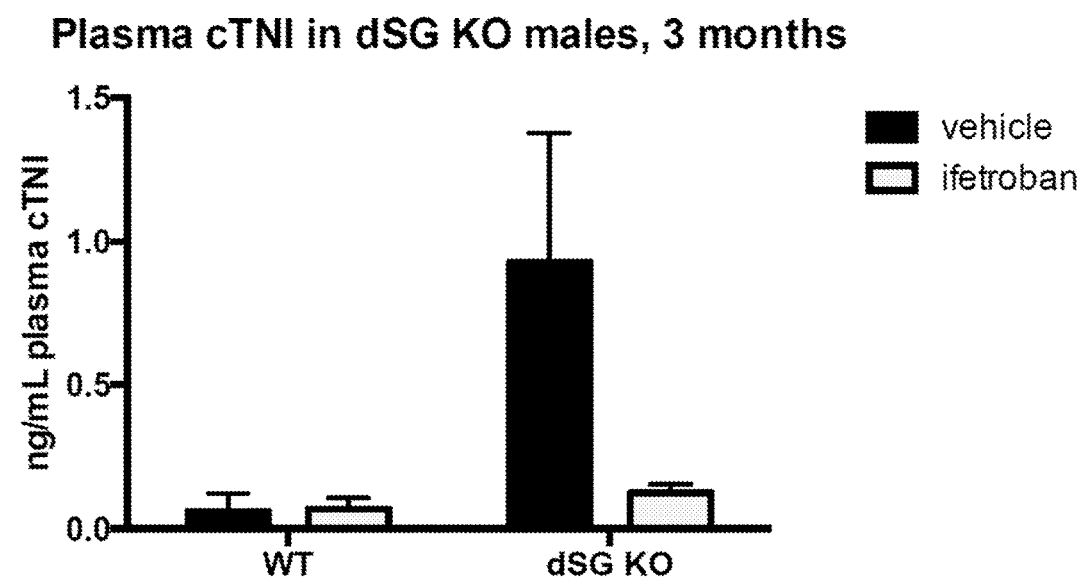
FIG. 2 is a graph showing plasma cTNI in dSG KO males at 3 months (vehicle-treated versus ifetroban-treated)

FIG. 2 shows plasma cTNI in dSG KO males at 3 months. The term "cTNI" means plasma cardiac troponin I. The term "KO" means knockout. The term "dSG" means Delta sarcoglycan. The term "WT" means wildtype. Plasma cardiac troponin I (cTNI) is highly specific and sensitive for myocardial tissue and can be measured rapidly. It is a reliable biomarker for cardiac damage. In FIG. 2, it can be seen that the plams cTNI levels are much higher in dSG KO mice than in WT mice.

Figure 3:
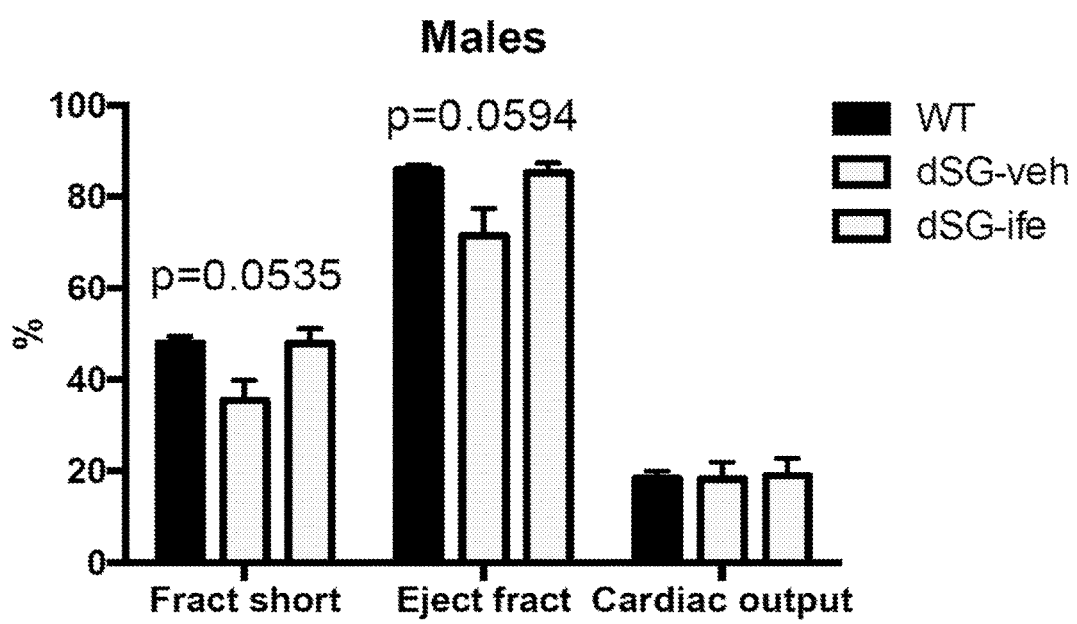
FIG. 3 is a graph showing 3 month Echo data in mice (WT(wild-type), dSG-vehicle and dSG-ifetroban treated)

FIG. 3 provides 3 month Echo data. The results shown therein demonstrate that at 3 months dSG KO males show cardiac dysfunction and ifetroban prevents cardiac dysfunction.

Figure 4:
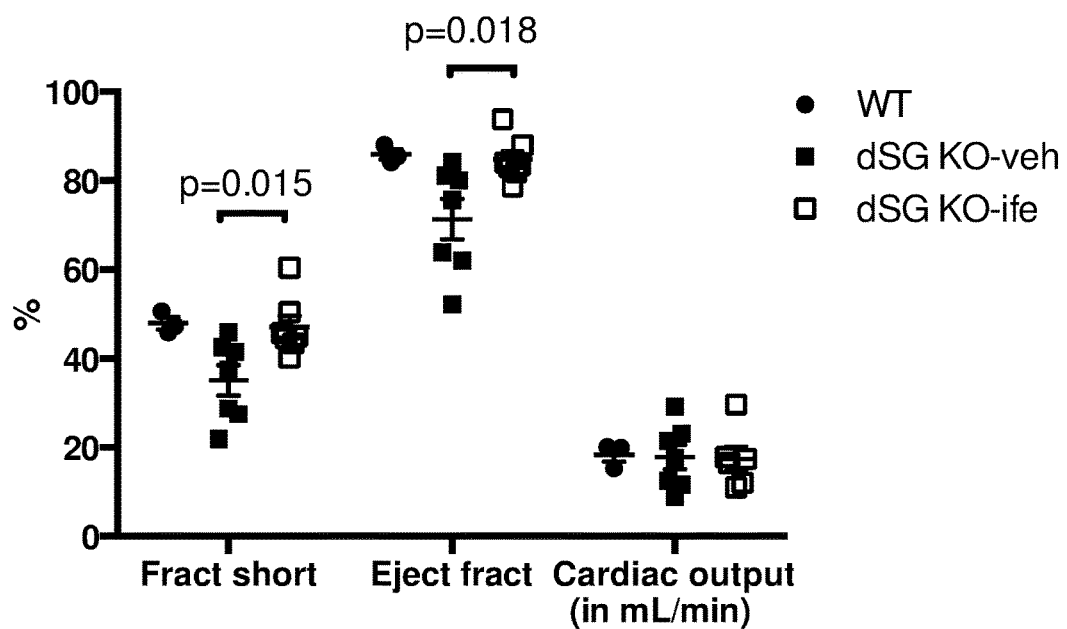
FIG. 4 is a graph providing cardiac output data for male mice at 3 months (WT, dSG KO-vehicle and dSG KO-ifetroban treated)

FIG. 4 provides cardiac output data for male dSG KO mice at 3 months. FIG. 4 shows that the dSG KO mice treated with ifetroban have improved cardiac dysfunction compared to vehicle. The cardiac function improved similar to WT levels.

Figure 5:
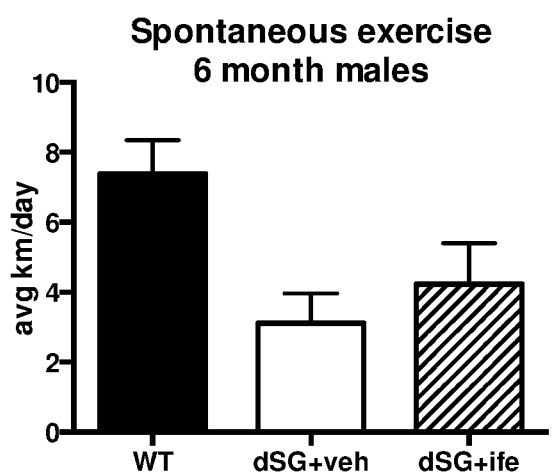
FIG. 5 is a graph providing spontaneous exercise data for 6 month old males (WT, dSG-vehicle and dSG-ifetroban treated)

FIG. 5 provides spontaneous exercise date for 6 month old males. The exercise was voluntary wheel running-free access to the wheel for 10 days after 4.5M of treatment. Males demonstrate a skeletal function deficit at 6M that is seen to a less extent in ifetroban-treated DSG KO mice. No difference is seen in females who run more compared to males regardless of genotype.

Figure 6:
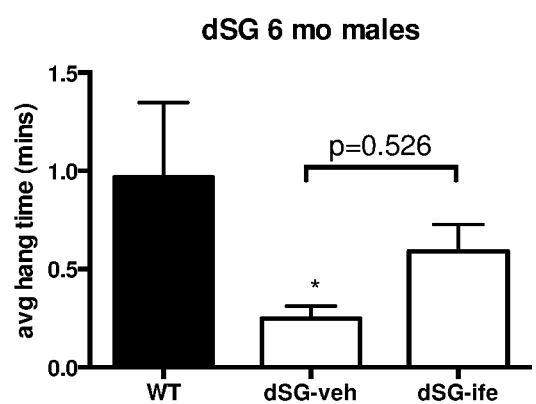
FIG. 6 is a graph showing average wire hang time in male mice at 6 months (WT, dSG-vehicle and dSG-ifetroban treated)

FIG. 6 shows wire hang in dSG mice at 6 months. An improved wire hang time is apparent in the dSG mice treated with ifetroban. *p<0.05 from WT by one-way ANOVA followed by Dunnett's multiple comparison post-test. Veh and ife-treated groups were NS tested against each other. N in parentheses. "ife"=ifetroban.

Figure 7:
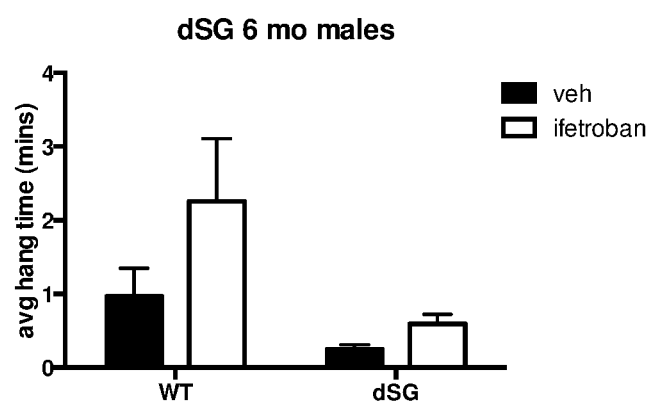
FIG. 7 is a graph showing the results of a wire hanging experiment (average hang Lime) at 6 months (WT, dSG; vehicle versus ifetroban-treated; P=0.0056 for genotype by 2-way ANOVA)

FIG. 7 shows the results of a wire hanging experiment at 6 months, with the average hang time plotted for dSG and WT mice.

Figure 8:
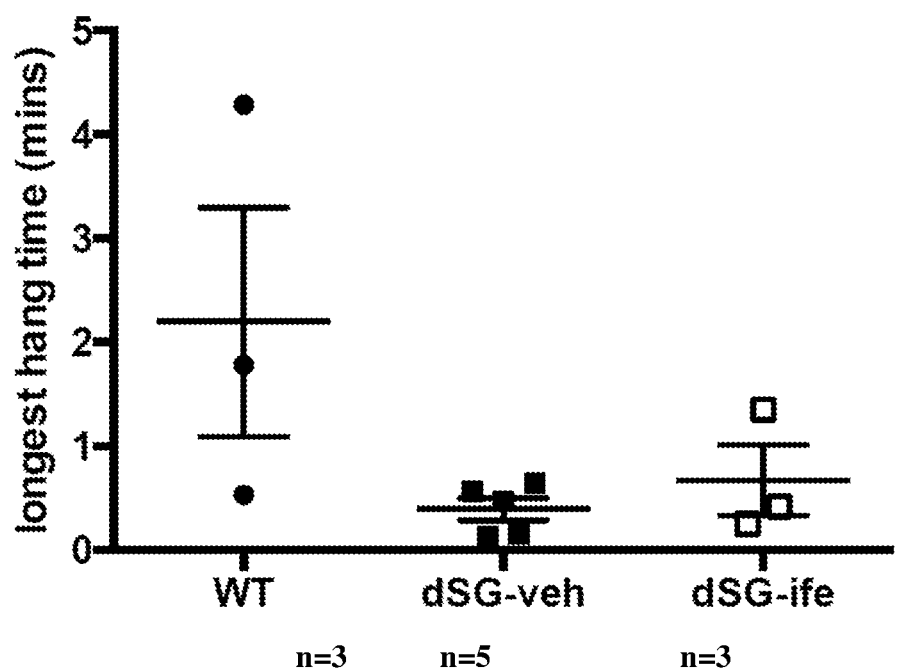
FIG. 8 is a graph showing 6 month wire hang time (longest time) for male mice tested (WT, dSG-vehicle, dSG-ifetroban treated)

FIG. 8 depicts wire hang time for mice tested. Male mice do not hang for a long time compared to females. It was difficult to measure any difference caused by ifetroban if any.

Figure 9A:
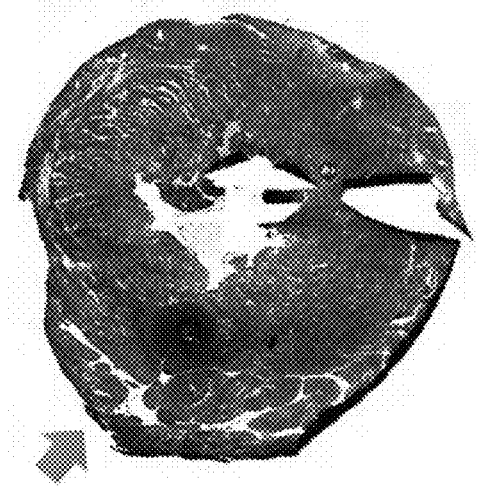
FIGS. 9A (dSGKO-vehicle) and 9B (DsGKO-ifetroban) show cardiac histology in dSG KO males. Less fibrosis seen in ifetroban treated RV. Shown is Masson's trichrome at 4× for gross histology. All tears/folds/red hotspots from slice preparation and not pathology. Some RV may also be affected by slicing (arrows).
Figure 9B:
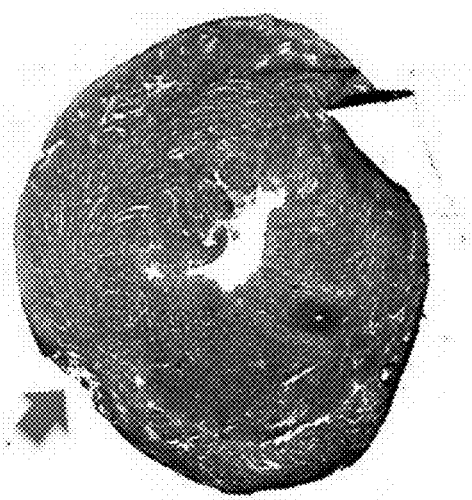

FIGS. 9A (dSGKO-vehicle) and 9B (DsGKO-ifetroban) show cardiac histology in dSG KO males. Less fibrosis seen in ifetroban treated RV. Shown is Masson's trichrome at 4× for gross histology. All tears/folds/red hotspots from slice preparation and not pathology. Some RV may also be affected by slicing (arrows).

FIGS. 10A(dSG-Veh), 10B(dSG-veh), 10C(dSG-ifetroban) and 10D(dSG-ifetroban) show cardiac histology in dSG KO males (using Masson's trichrome, 2×). It can be seen that there is less fibrosis in the ifetroban treated RV. RV=right ventricle.

FIGS. 11A1, 11A2, 11A3 and 11A4 shows cardiac histology in dSG KO males (using Masson's trichrome, 10×) in the left ventricle (11A1=mouse #1, dSG KO-vehicle; 11A2=mouse #2, dSG KO-vehicle; 11A3=mouse #1, dSG KO-ifetroban; and 11A4=mouse #2, dSG KO-ifetroban); FIGS. 11B1, 11B2, 11B3 and 11B14 shows cardiac histology in the right ventricle (11B1=mouse #1, dSG KO-vehicle; 11B2=mouse #2, dSG KO-vehicle; 11B3=mouse #1, dSG KO-ifetroban; and 11B4=mouse #2, dSG KO-ifetroban). LV=left ventricle; RV=right ventricle. Less fibrosis was seen in ifetroban-treated KO mice.

FIGS. 12A(WT1), 12B(dSG-KO-vehicle), 12C(WT2) and 12D(dSG-KO-ifetroban) shows skeletal muscle histology in WT and dSG KO males (tibialis cross-section, using Masson's trichrome). Some fibrosis may be due to specific section of muscle.

FIGS. 13A(WT-vehicle), 13B(WT-ifetroban), 13C(dSG KO-vehicle) and 13D(dSG-KO-ifetroban) are cross-sections of intestinal tissue showing that ifetroban may prevent the loss of intestinal smooth muscle in the large intestine Muscularis. The DSG KO mice were missing smooth muscle (especially missing longitudinal smooth muscle) while ifetroban-treated mice have similar sections to WT smooth muscle. "H&E"=Hematoxylin & eosin.

FIG. 13 shows that ifetroban-treated dSG KO mice have less fibrosis than vehicle-treated dSG KO mice.

FIGS. 14A and 14B are graphs showing the percent survival of dSG KO males (14A) and dSG females (14B) treated with ifetroban or vehicle.

Figure 15:
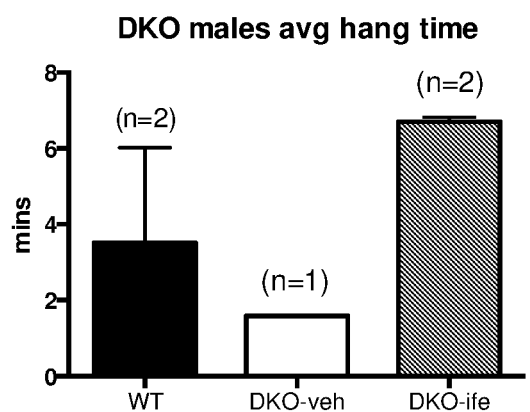
FIG. 15 are graphs showing wire hang in WT and DKO males at 10 weeks (ifetroban-treated ("ife") versus vehicle)

FIG. 15 are graphs showing wire hang in DKO males at 10 weeks (ifetroban-treated ("ife") versus vehicle). The results show that the ifetroban-treated mice had significantly longer average hang times than mice treated with vehicle.

Figure 16:
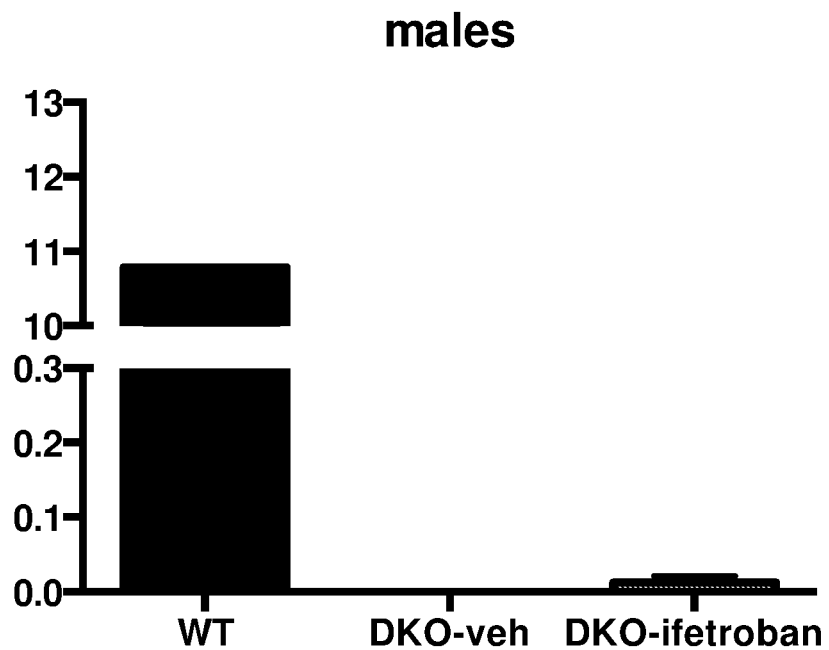
FIG. 16 is a graph showing spontaneous running in WT and DKO mice measured from 9-10 weeks (DKO-vehicle and DKO-ifetroban treated)

FIG. 16 shows spontaneous running in DKO mice: measured from 9-10 weeks.

Figure 17:
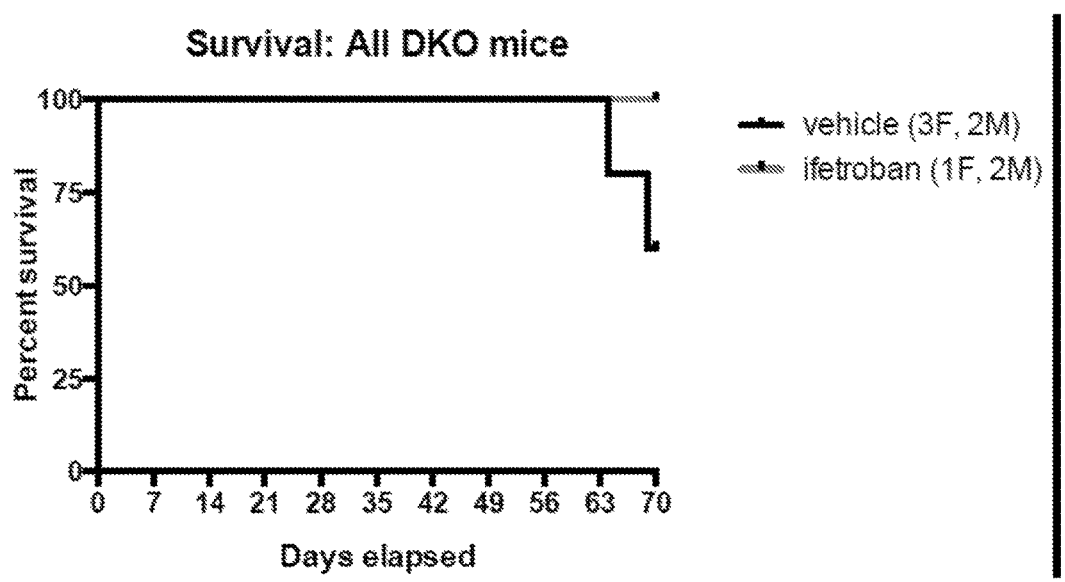
FIG. 17 is a graph showing survival for all DKO mice (vehicle and ifetroban treated).

FIG. 17 shows survival for all DKO mice. The ifetroban-treated mice survived beyond 70 days, while the vehicle-treated mice (both male and female) did not.

CONCLUSION

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A method of treating Duchenne muscular dystrophy in a patient in need of treatment thereof, comprising administering a therapeutically effective amount of a thromboxane $A_2$ receptor antagonist to the patient, wherein the thromboxane $A_2$ receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), or a pharmaceutically acceptable salt thereof.

2. The method of claim 1, further comprising administering the thromboxane $A_2$ antagonist to the patient on a chronic basis.

3. The method of claim 1, wherein the thromboxane $A_2$ receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium).

4. The method of claim 1, wherein the thromboxane $A_2$ receptor antagonist is administered orally, intranasally, rectally, vaginally, sublingually, buccally, parenterally, or transdermally.

5. The method of claim 1, wherein the thromboxane $A_2$ receptor antagonist is administered parenterally.

6. The method of claim 1, wherein the thromboxane A₂ receptor antagonist is administered orally.

7. The method of claim 2, wherein the thromboxane A₂ receptor antagonist is administered prophylactically to prevent cardiomyopathy in the patient.

8. The method of claim 2, wherein the thromboxane A₂ receptor antagonist is administered prophylactically to prevent gastrointestinal dysfunction in the patient.

9. The method of claim 1, wherein the therapeutically effective amount is from 50 mg to 500 mg per day.

10. The method of claim 1, wherein the therapeutically effective amount is from 150 mg to 350 mg per day and the ifetroban or pharmaceutically acceptable salt thereof is administered orally.

11. A method of treating cardiac dysfunction in a human patient suffering from muscular dystrophy, comprising administering a therapeutically effective amount of a thromboxane A₂ receptor antagonist to the human patient, wherein the thromboxane A₂ receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), or a pharmaceutically acceptable salt thereof.

12. The method of claim 11, wherein the therapeutically effective amount is from 50 mg to 500 mg per day.

13. The method of claim 11, wherein the thromboxane A₂ receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium).

14. The method of claim 11, wherein the therapeutically effective amount is from 150 mg to 350 mg per day and the ifetroban or pharmaceutically acceptable salt thereof is administered orally.

15. The method of claim 1, wherein the thromboxane A₂ receptor antagonist is administered orally once per day.

16. The method of claim 15, wherein the therapeutically effective amount is 50 mg.

17. The method of claim 15, wherein the therapeutically effective amount is 100 mg.

18. The method of claim 15, wherein the therapeutically effective amount is 150 mg.

19. The method of claim 15, wherein the therapeutically effective amount is 300 mg.

20. The method of claim 11, wherein the thromboxane A₂ receptor antagonist is administered orally once per day.

* * * * *

UNITED STATES PATENT AND TRADEMARK OFFICE
CERTIFICATE OF CORRECTION

PATENT NO. : 10,456,380 B2  
APPLICATION NO. : 16/240368  
DATED : October 29, 2019  
INVENTOR(S) : Leo Pavliv et al.

Page 1 of 1

It is certified that error appears in the above-identified patent and that said Letters Patent is hereby corrected as shown below:

In the Specification

Column 1, Lines 6-8, "This invention was made with government support under grant numbers R01HL095797 and P01HL108800 awarded by the National Institutes of Health." should read "This invention was made with government support under grant numbers HL135011, HL095797 and HL108800 awarded by the National Institutes of Health."

Signed and Sealed this  
Thirtieth Day of September, 2025

John A. Squires  
*Director of the United States Patent and Trademark Office*